(12) United States Patent
Ma et al.

(10) Patent No.: US 11,974,993 B2
(45) Date of Patent: May 7, 2024

(54) SOLUTION FORMULATIONS OF CX-011

(71) Applicant: City of Hope, Duarte, CA (US)

(72) Inventors: Yuelong Ma, Glendora, CA (US); Rajiv Nallu, Duarte, CA (US); David Horne, Altadena, CA (US)

(73) Assignee: City of Hope, Duarte, CA (US)

( * ) Notice: Subject to any disclaimer, the term of this patent is extended or adjusted under 35 U.S.C. 154(b) by 0 days.

(21) Appl. No.: 17/677,408

(22) Filed: Feb. 22, 2022

(65) Prior Publication Data

US 2022/0273635 A1    Sep. 1, 2022

Related U.S. Application Data

(60) Provisional application No. 63/155,223, filed on Mar. 1, 2021.

(51) Int. Cl.
*A61K 31/4439*    (2006.01)
*A61K 9/08*    (2006.01)
*A61K 47/44*    (2017.01)

(52) U.S. Cl.
CPC ............ *A61K 31/4439* (2013.01); *A61K 9/08* (2013.01); *A61K 47/44* (2013.01)

(58) Field of Classification Search
CPC ....... A61K 31/4439; A61K 9/08; A61K 47/44
See application file for complete search history.

(56) References Cited

U.S. PATENT DOCUMENTS 4,522,811 A    6/1985    Eppstein et al.
2020/0377494 A1*    12/2020    Evseenko ............ A61K 9/0019

FOREIGN PATENT DOCUMENTS

| WO | WO-2018150182 A1 * | 8/2018 | ............. A61K 31/05 |
| WO | WO-2019084470 A1 * | 5/2019 | ............. A61K 45/06 |
| WO | WO-2020206258 A1 * | 10/2020 | ............. A61K 31/05 |

OTHER PUBLICATIONS

Bioorg Med Chem. 2013, 21,6385-97 (Year: 2013).*

* cited by examiner

*Primary Examiner* — Theodore R. Howell
*Assistant Examiner* — Manahil Mirghani Ali Abdalhameed
(74) *Attorney, Agent, or Firm* — MINTZ, LEVIN, COHN, FERRIS, GLOVSKY AND POPEO, P.C.

(57) ABSTRACT

Provided herein are solution formulations of CX-011 and related methods for making solution formulations of CX-011. Also provided are methods of treating an inflammatory disorder, such as osteoarthritis, or cancer in a subject in need thereof by administering an effective amount of the solution formulations of CX-011.

22 Claims, No Drawings

SOLUTION FORMULATIONS OF CX-011

CROSS-REFERENCES TO RELATED APPLICATIONS

This application claims priority to U.S. Provisional Application No. 63/155,223, filed Mar. 1, 2021, the content of which is incorporated by reference in its entirety.

BACKGROUND OF THE INVENTION

CX-011 is a compound useful for treating disease and disorders associated with gp130 activity, particularly those associated with inflammation. However, the compound has poor solubility in aqueous solution and efforts to render it soluble were unfruitful.

Suspensions of insoluble compounds may not be efficacious and may not be rendered acceptable for injection by sterile filtration. Consequently, there is a need for formulations that solubilize compounds in solution.

BRIEF SUMMARY OF THE INVENTION

In an aspect, provided herein are formulation comprising CX-011 in solution, wherein CX-011 has the formula:

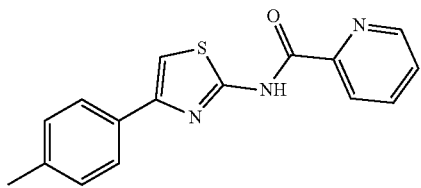

In aspects the solution includes a non-ionic surfactant. In aspects, the solution is an aqueous solution. Also provided are methods of making said formulations.

In an aspect, also provided herein are methods of reducing activation of gp130 in a subject in need thereof by administering an effective amount of the disclosed formulations. Also provided herein are methods of treating an inflammatory disease or cancer in a subject by administering an effective amount of the disclosed formulations.

DETAILED DESCRIPTION OF THE INVENTION

Provided herein are aqueous solution formulations of CX-011 and related methods thereof. In some embodiments the formulations include non-ionic surfactants. The non-ionic surfactants can include Polyoxyl 15 Hydroxystearate, Polyoxyl castor oil, PEG-35 Castor Oil, PEG-40 Hydrogenated Castor Oil, PEG-60 Hydrogenated Castor Oil, Polysorbate 80, Polysorbate 60, Polysorbate 40, or Polysorbate 20. These aqueous formulations are amenable to sterile filtration.

In this disclosure, "comprises," "comprising," "containing" and "having" and the like can have the meaning ascribed to them in U.S. patent law and can mean "includes," "including," and the like. "Consisting essentially of or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

As used herein "CX-011" refers to the compound with the structure as shown below:

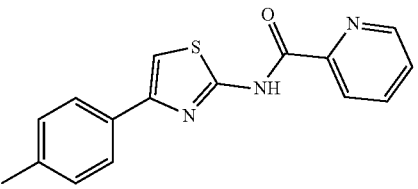 [SMILES: Cc1ccc(-c2csc(NC(=O)c3ccccn3)n2)cc1]

CX-011 is disclosed in U.S. Patent Publication No. 2020/0377494A1, hereby incorporated by reference, and is an analog of a compound, RCGD 423, from screening a library of 170,000 compounds for gp130 signalling. CX-011 almost completely blocked the generation of aggrecan and collagen neoepitopes, indicative of strong anti-catabolic potential, and did not increase levels of pSTAT3 and MYC.

However, CX-011 is poorly soluble in aqueous solution and nanoemulsions cannot be sterile filtered. "Soluble" is used in accordance with its plain ordinary meaning and refers to the ability of a solid compound (solute) to dissolve in a liquid. In embodiments the liquid is aqueous, i.e. the solvent is water.

A "non-ionic surfactant" is used in accordance with its plain ordinary meaning and refers to any of a class of synthetic detergents (as long-chain ether derivatives or esters of alcohols or phenols) that are neither anionic nor cationic but produce electrically neutral colloidal particles in solution. Non-ionic surfactants have covalently bonded oxygen-containing hydrophilic groups, which are bonded to hydrophobic parent structures. Non-ionic surfactants include terminally blocked ethoxylates such as poloxamers, polysorbates, ethoxylates, fatty alcohol ethoxylates, alkylphenol ethoxylates, fatty acid ethoxylates, fatty acid ethoxylates, special ethoxylated fatty esters and oils, ethoxylated amines and/or fatty acid amides, fatty acid esters of polyhydroxy compounds, fatty acid esters of glycerol, fatty acid esters of sucrose, and alkyl polyglucosides. The non-ionic surfactant can be a mixture of polyglycolated mono or di-ester of hydroxyl fatty acid and free polyethylene glycol.

Poloxamers are nonionic triblock copolymers composed of a central hydrophobic chain of polyoxypropylene (poly(propylene oxide)) flanked by two hydrophilic chains of polyoxyethylene (poly(ethylene oxide)). Because the lengths of the polymer blocks can be customized, many different poloxamers exist that have slightly different properties. For the generic term poloxamer, these copolymers are commonly named with the letter P (for poloxamer) followed by three digits: the first two digits multiplied by 100 give the approximate molecular mass of the polyoxypropylene core, and the last digit multiplied by 10 gives the percentage polyoxyethylene content (e.g. P407=poloxamer with a polyoxypropylene molecular mass of 4000 g/mo} and a 70% polyoxyethylene content). For the Pluronic and Synperonic tradenames, coding of these copolymers starts with a letter to define its physical form at room temperature (L=liquid, P=paste, F=flake (solid)) followed by two or three digits, The first digit (two digits in a three-digit number) in the numerical designation, multiplied by 300, indicates the approximate molecular weight of the hydrophobe; and the last digit×10 gives the percentage polyoxyethylene content (e.g., L61 indicates a polyoxypropylene molecular mass of 1800 g/mol and a 10% polyoxyethylene content). For example, poloxamer 181 (P181)=Pluronic L61 and Synperonic PE/L 61. Poloxamers include polyoxyl 15 hydroxystearate (Kolliphor HS 15), PEG-35 Castor Oil (Kolliphor® EL), PEG-40 Hydrogenated Castor Oil (Kolliphor® RH 40), and PEG-60 Hydrogenated Castor Oil (Kolliphor® RH 60).

Polysorbates are fatty acid esters of sorbitol and include sorbitan monolaurate, sorbitan monostearate, and sorbitan tristearate. Polysorbates can include polysorbate 20 (polyoxyethylene (20) sorbitan monolaurate) (Tween 20), Polysorbate 40 (polyoxyethylene (20) sorbitan monopalmitate) (Tween 40), polysorbate 60 (polyoxyethylene (20) sorbitan monostearate) (Tween 60), and polysorbate 80 (polyoxyethylene (20) sorbitan monooleate) (Tween 80).

"Pharmaceutically acceptable excipient" and "pharmaceutically acceptable carrier" refer to a substance that aids the administration of an active agent to and absorption by a subject and can be included in the compositions of the present disclosure without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the disclosure. One of skill in the art will recognize that other pharmaceutical excipients are useful in the present disclosure.

As used herein, the term "about" means a range of values including the specified value, which a person of ordinary skill in the art would consider reasonably similar to the specified value. In embodiments, about means within a standard deviation using measurements generally acceptable in the art. In embodiments, about means a range extending to +/−10% of the specified value. In embodiments, about includes the specified value.

As used herein, the term "inflammatory disease" refers to a disease or condition characterized by aberrant inflammation (e.g. an increased level of inflammation compared to a control such as a healthy person not suffering from a disease). Examples of inflammatory diseases include autoimmune diseases, arthritis, rheumatoid arthritis, osteoarthritis, psoriatic arthritis, juvenile idiopathic arthritis, multiple sclerosis, systemic lupus erythematosus (SLE), myasthenia gravis, juvenile onset diabetes, diabetes mellitus type 1, graft-versus-host disease (GvHD), Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves ophthalmopathy, inflammatory bowel disease, Addison's disease, Vitiligo, asthma, allergic asthma, acne vulgaris, celiac disease, chronic prostatitis, inflammatory bowel disease, pelvic inflammatory disease, reperfusion injury, ischemia reperfusion injury, stroke, sarcoidosis, transplant rejection, interstitial cystitis, atherosclerosis, scleroderma, and atopic dermatitis.

Examples of inflammatory disease include osteoarthritis of the knee or temporomandibular joint osteoarthritis.

As used herein, the term "cancer" refers to all types of cancer, neoplasm or malignant tumors found in mammals (e.g. humans), including leukemias, lymphomas, carcinomas and sarcomas. Exemplary cancers that may be treated with a compound or method provided herein include brain cancer, glioma, glioblastoma, neuroblastoma, prostate cancer, colorectal cancer, pancreatic cancer, Medulloblastoma, melanoma, cervical cancer, gastric cancer, ovarian cancer, lung cancer, cancer of the head, Hodgkin's Disease, and Non-Hodgkin's Lymphomas. Exemplary cancers that may be treated with a compound or method provided herein include cancer of the thyroid, endocrine system, brain, breast, cervix, colon, head & neck, liver, kidney, lung, ovary, pancreas, rectum, stomach, and uterus. Additional examples include, thyroid carcinoma, cholangiocarcinoma, pancreatic adenocarcinoma, skin cutaneous melanoma, colon adenocarcinoma, rectum adenocarcinoma, stomach adenocarcinoma, esophageal carcinoma, head and neck squamous cell carcinoma, breast invasive carcinoma, lung adenocarcinoma, lung squamous cell carcinoma, non-small cell lung carcinoma, mesothelioma, multiple myeloma, neuroblastoma, glioma, glioblastoma multiforme, ovarian cancer, rhabdomyosarcoma, primary thrombocytosis, primary macroglobulinemia, primary brain tumors, malignant pancreatic insulanoma, malignant carcinoid, urinary bladder cancer, premalignant skin lesions, testicular cancer, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

As used herein, the term "autoimmune disease" refers to a disease or condition in which a subject's immune system has an aberrant immune response against a substance that does not normally elicit an immune response in a healthy subject. Examples of autoimmune diseases that may be treated with a compound, pharmaceutical composition, or method described herein include Acute Disseminated Encephalomyelitis (ADEM), Acute necrotizing hemorrhagic leukoencephalitis, Addison's disease, Agammaglobulinemia, Alopecia areata, Amyloidosis, Ankylosing spondylitis, Anti-GBM/Anti-TBM nephritis, Antiphospholipid syndrome (APS), Autoimmune angioedema, Autoimmune aplastic anemia, Autoimmune dysautonomia, Autoimmune hepatitis, Autoimmune hyperlipidemia, Autoimmune immunodeficiency, Autoimmune inner ear disease (AIED), Autoimmune myocarditis, Autoimmune oophoritis, Autoimmune pancreatitis, Autoimmune retinopathy, Autoimmune thrombocytopenic purpura (ATP), Autoimmune thyroid disease, Autoimmune urticaria, Axonal or neuronal neuropathies, Balo disease, Behcet's disease, Bullous pemphigoid, Cardiomyopathy, Castleman disease, Celiac disease, Chagas disease, Chronic fatigue syndrome, Chronic inflammatory demyelinating polyneuropathy (CIDP), Chronic recurrent multifocal ostomyelitis (CRMO), Churg-Strauss syndrome, Cicatricial pemphigoid/benign mucosal pemphigoid, Crohn's disease, Cogans syndrome, Cold agglutinin disease, Congenital heart block, Coxsackie myocarditis, CREST disease, Essential mixed cryoglobulinemia, Demyelinating neuropathies, Dermatitis herpetiformis, Dermatomyositis, Devic's disease (neuromyelitis optica), Discoid lupus, Dressler's syndrome, Endometriosis, Eosinophilic esophagitis, Eosinophilic fasciitis, Erythema nodosum, Experimental allergic encephalomyelitis, Evans syndrome, Fibromyalgia, Fibrosing alveolitis, Giant cell arteritis (temporal arteritis), Giant cell myocarditis, Glomerulonephritis, Goodpasture's syndrome, Granulomatosis with Polyangiitis (GPA) (formerly called Wegener's Granulomatosis), Graves' disease, Guillain-Barre syndrome, Hashimoto's encephalitis, Hashimoto's thyroiditis, Hemolytic anemia, Henoch-Schonlein purpura, Herpes gestationis, Hypogammaglobulinemia, Idiopathic thrombocytopenic purpura (ITP), IgA nephropathy, IgG4-related sclerosing disease, Immunoregulatory lipoproteins, Inclusion body myositis, Interstitial cystitis, Juvenile arthritis, Juvenile diabetes (Type 1 diabetes), Juvenile myositis, Kawasaki syndrome, Lambert-Eaton syndrome, Leukocytoclastic vasculitis, Lichen planus, Lichen sclerosus, Ligneous conjunctivitis, Linear IgA disease (LAD), Lupus (SLE), Lyme disease, chronic, Meniere's disease, Microscopic polyangiitis, Mixed connective tissue disease (MCTD), Mooren's ulcer, Mucha-Habermann disease, Multiple sclerosis, Myasthenia gravis, Myositis, Narcolepsy, Neuromyelitis optica (Devic's), Neutropenia, Ocular cicatricial pemphigoid, Optic neuritis, Palindromic rheumatism, PANDAS (Pediatric Autoimmune Neuropsychiatric Disorders Associated with Streptococcus), Paraneoplastic cerebellar degeneration, Paroxysmal nocturnal hemoglobinuria (PNH), Parry Romberg syndrome, Parsonnage-Turner syndrome, Pars planitis (peripheral uveitis), Pemphigus, Peripheral neuropathy, Perivenous encephalomyelitis, Pernicious anemia, POEMS syndrome, Polyarteritis nodosa, Type I, II, & III autoimmune polyglandular syndromes, Polymyalgia rheumatica, Polymyositis, Postmyocardial infarction syndrome, Postpericardiotomy syndrome, Progesterone dermatitis, Primary biliary cirrhosis, Primary sclerosing cholangitis, Psoriasis, Psoriatic arthritis, Idiopathic pulmonary fibrosis, Pyoderma gangrenosum, Pure red cell aplasia, Raynauds phenomenon, Reactive Arthritis, Reflex sympathetic dystrophy, Reiter's syndrome, Relapsing polychondritis, Restless legs syndrome, Retroperitoneal fibrosis, Rheumatic fever, Rheumatoid arthritis, Sarcoidosis, Schmidt syndrome, Scleritis, Scleroderma, Sjogren's syndrome, Sperm & testicular autoimmunity, Stiff person syndrome, Subacute bacterial endocarditis (SBE), Susac's syndrome, Sympathetic ophthalmia, Takayasu's arteritis, Temporal arteritis/Giant cell arteritis, Thrombocytopenic purpura (TTP), Tolosa-Hunt syndrome, Transverse myelitis, Type 1 diabetes, Ulcerative colitis, Undifferentiated connective tissue disease (UCTD), Uveitis, Vasculitis, Vesiculobullous dermatosis, Vitiligo, or Wegener's granulomatosis (i.e., Granulomatosis with Polyangiitis (GPA).

"Treating" or "treatment" as used herein (and as well-understood in the art) also broadly includes any approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delay or slowing of disease progression, amelioration or palliation of the disease state, diminishment of the reoccurrence of disease, and remission, whether partial or total and whether detectable or undetectable. In other words, "treatment" as used herein includes any cure, amelioration, or prevention of a disease. Treatment may prevent the disease from occurring; inhibit the disease's spread; relieve the disease's symptoms, fully or partially remove the disease's underlying cause, shorten a disease's duration, or do a combination of these things.

"Treating" and "treatment" as used herein include prophylactic treatment. Treatment methods include administering to a subject a therapeutically effective amount of an active agent. The administering step may consist of a single administration or may include a series of administrations. The length of the treatment period depends on a variety of factors, such as the severity of the condition, the age of the patient, the concentration of active agent, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In some instances, chronic administration may be required. For example, the compositions are administered to the subject in an amount and for a duration sufficient to treat the patient. In embodiments, the treating or treatment is no prophylactic treatment.

The term "prevent" refers to a decrease in the occurrence of disease symptoms in a patient. As indicated above, the prevention may be complete (no detectable symptoms) or partial, such that fewer symptoms are observed than would likely occur absent treatment.

"Patient" or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

An "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). In embodiments, the reduction is a reduction in inflammation. A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

As used herein, the term "administering" means, for example, oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). In embodiments, the administration is oral administration. Parenteral administration includes, e.g., intravenous, intramuscular, intra-arteriole, intradermal, intraarticular, subcutaneous, intraperitoneal, intraventricular, and intracranial. As used herein, "intraarticular administration" means administration directly into the joints to reduce inflammation. Other modes of delivery include, but are not limited to, the use of liposomal formulations, intravenous infusion, transdermal patches, etc. In embodiments, the administering does not include administration of any active agent other than the recited active agent.

By "co-administer" it is meant that a composition described herein is administered at the same time, just prior to, or just after the administration of one or more additional therapies. The compounds provided herein can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present disclosure can be delivered transdermally, by a topical route, or formulated as applicator sticks, solutions, suspensions, emulsions, gels, creams, ointments, pastes, jellies, paints, powders, and aerosols.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells. Prokaryotic cells include but are not limited to bacteria. Eukaryotic cells include but are not limited to yeast cells and cells derived from plants and animals, for example mammalian, insect (e.g., spodoptera) and human cells. Cells may be useful when they are naturally nonadherent or have been treated not to adhere to surfaces, for example by trypsinization.

The terms "immune response" and the like refer, in the usual and customary sense, to a response by an organism that protects against disease. The response can be mounted by the innate immune system or by the adaptive immune system, as well known in the art.

The terms "modulating immune response" and the like refer to a change in the immune response of a subject as a consequence of administration of an agent, e.g., a compound as disclosed herein, including embodiments thereof. Accordingly, an immune response can be activated or deactivated as a consequence of administration of an agent, e.g., a compound as disclosed herein, including embodiments thereof.

Formulations

Provided herein are formulations of CX-011 that render the compound soluble in an aqueous solution. In embodiments, the formulation includes a non-ionic surfactant. In embodiments the non-ionic surfactant includes a terminally blocked ethoxylate, a polysorbate, an ethoxylate, a fatty alcohol ethoxylate, an alkylphenol ethoxylate, a fatty acid ethoxylate, special ethoxylated fatty esters and oils, ethoxylated amines and/or fatty acid amides, fatty acid esters of polyhydroxy compounds, a fatty acid ester of glycerol, a fatty acid ester of sucrose, or an alkyl polyglucoside. In embodiments that non-ionic surfactant is a terminally blocked ethoxylate. In embodiments that non-ionic surfactant is a polysorbate. In embodiments that non-ionic surfactant is an ethoxylate. In embodiments that non-ionic surfactant is a fatty alcohol ethoxylate. In embodiments that non-ionic surfactant is an alkylphenol ethoxylate. In embodiments that non-ionic surfactant is a fatty acid ethoxylate. In embodiments that non-ionic surfactant is special ethoxylated fatty esters and oils. In embodiments that non-ionic surfactant is ethoxylated amines and/or fatty acid amides. In embodiments that non-ionic surfactant is fatty acid esters of polyhydroxy compounds. In embodiments that non-ionic surfactant is a fatty acid ester of glycerol. In embodiments that non-ionic surfactant is a fatty acid ester of sucrose. In embodiments that non-ionic surfactant is an alkyl polyglucoside. In embodiments, the non-ionic surfactant is a mixture of polyglycolated mono or di-ester of hydroxyl fatty acid and free polyethylene glycol.

In embodiments the non-ionic surfactant is a poloxamer. In embodiments the non-ionic surfactant is polyoxyl 15 hydroxystearate (Kolliphor HS 15), PEG-35 Castor Oil (Kolliphor® EL), PEG-40 Hydrogenated Castor Oil (Kolliphor® RH 40), or PEG-60 Hydrogenated Castor Oil (Kolliphor® RH 60). In embodiments the non-ionic surfactant is polyoxyl 15 hydroxystearate (Kolliphor HS 15). In embodiments the non-ionic surfactant is PEG-35 Castor Oil (Kolliphor® EL). In embodiments the non-ionic surfactant is PEG-40 Hydrogenated Castor Oil (Kolliphor® RH 40). In embodiments the non-ionic surfactant is PEG-60 Hydrogenated Castor Oil (Kolliphor® RH 60).

In embodiments the non-ionic surfactant is a polysorbate. In embodiments the non-ionic surfactant is polysorbate 20 (polyoxyethylene (20) sorbitan monolaurate) (Tween 20), Polysorbate 40 (polyoxyethylene (20) sorbitan monopalmitate) (Tween 40), polysorbate 60 (polyoxyethylene (20) sorbitan monostearate) (Tween 60), or polysorbate 80 (polyoxyethylene (20) sorbitan monooleate) (Tween 80). In embodiments the non-ionic surfactant is polysorbate 20 (polyoxyethylene (20) sorbitan monolaurate) (Tween 20). In embodiments the non-ionic surfactant is Polysorbate 40 (polyoxyethylene (20) sorbitan monopalmitate) (Tween 40). In embodiments the non-ionic surfactant is polysorbate 60 (polyoxyethylene (20) sorbitan monostearate) (Tween 60). In embodiments the non-ionic surfactant is polysorbate 80 (polyoxyethylene (20) sorbitan monooleate) (Tween 80).

In embodiments, the formulation comprises from about 1.0 µg/ml of CX-011 to about 5,000.00 µg/ml of CX-011. In embodiments, the formulation comprises at least about 150 µg/ml CX-011. In embodiments, the formulation comprises at least about 1.5 µg/ml of CX-011. In embodiments, the formulation comprises at least about 5 µg/ml of CX-011. In embodiments, the formulation comprises at least about 25 µg/ml of CX-011. In embodiments, the formulation comprises at least about 50 µg/ml of CX-011. In embodiments, the formulation comprises at least about 100 µg/ml of CX-011. In embodiments, the formulation comprises at least about 200 µg/ml CX-011. In embodiments, the formulation comprises at least about 300 µg/ml CX-011. In embodiments, the formulation comprises at least about 400 µg/ml CX-011. In embodiments, the formulation comprises at least about 500 µg/ml CX-011. In embodiments, the formulation comprises at least about 1,000 µg/ml CX-011. In embodiments, the formulation comprises at least about 1500 µg/ml CX-011. In embodiments, the formulation comprises at least about 2,000 µg/ml CX-011. In embodiments, the formulation comprises at least about 2,500 µg/ml CX-011. In embodiments, the formulation comprises at least about 3,000 µg/ml CX-011. In embodiments, the formulation comprises at least about 3500 µg/ml CX-011. In embodiments, the formulation comprises at least about 4,000 µg/ml CX-011. In embodiments, the formulation comprises at least about 4,500 µg/ml CX-011. In embodiments, the formulation comprises at least about 4,800 µg/ml CX-011.

In embodiments, the concentration of non-ionic surfactant or combination of non-ionic surfactants in the aqueous formulation with CX-011 is between about 1 to about 15% (w/v). In embodiments, the concentration of non-ionic surfactant or combination of non-ionic surfactants in the formulation is between about 1 to about 10% (w/v). In embodiments, the concentration of non-ionic surfactant or combination of non-ionic surfactants in the formulation is between about 1 to about 9% (w/v). In embodiments, the concentration of non-ionic surfactant or combination of non-ionic surfactants in the formulation is between about 1 to about 8% (w/v). In embodiments, the concentration of non-ionic surfactant or combination of non-ionic surfactants in the formulation is between about 1 to about 7% (w/v). In embodiments, the concentration of non-ionic surfactant or combination of non-ionic surfactants in the formulation is between about 1 to about 6% (w/v). In embodiments, the concentration of non-ionic surfactant or combination of non-ionic surfactants in the formulation is between about 1 to about 5% (w/v). In embodiments, the concentration of non-ionic surfactant or combination of non-ionic surfactants in the formulation is between about 1 to about 4% (w/v). In embodiments, the concentration of non-ionic surfactant or combination of non-ionic surfactants in the formulation is between about 1 to about 3% (w/v). In embodiments, the concentration of non-ionic surfactant or combination of non-ionic surfactants in the formulation is between about 1.5 to about 3% (w/v). In embodiments, the concentration of non-ionic surfactant or combination of non-ionic surfactants in the formulation is between about 1.5 to about 2% (w/v).

In embodiments, the aqueous solution of CX-011 further includes one or more pharmaceutically acceptable excipients. "Pharmaceutically acceptable excipient" and "pharmaceutically acceptable carrier" refer to a substance that aids the administration of an active agent to and absorption by a subject and can be included in the compositions of the present disclosure without causing a significant adverse toxicological effect on the patient. Non-limiting examples of pharmaceutically acceptable excipients include NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethyl-cellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the disclosure. One of skill in the art will recognize that other pharmaceutical excipients are useful in the present disclosure.

In embodiments, provided herein are solutions of CX-011 (equal or more than 0.15 mg/mL) in Kolliphor HS 15 (1-3% w/v). In embodiments, the solution is an aqueous solution.

The solution can be filtered for sterilization in contrast to suspensions of CX-011. The solution can also be prepared in PBS, saline or other similar physiological buffers with pH range 5-8 with or without antibacterial agents.

A pharmaceutical composition of the disclosure is formulated to be compatible with its intended route of administration. Examples of routes of administration include parenteral, e.g., intravenous, intradermal, subcutaneous, oral (e.g., inhalation), transdermal (topical), transmucosal, and rectal administration. In embodiments, the administration is intraarticular. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. In embodiments, solutions or suspensions used for intraarticular application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy to administer by a syringe. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it is preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound, e.g. a compound disclosed herein, in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the methods of preparation are vacuum drying and freeze-drying which yields a powder of the active ingredient plus any additional desired ingredient from a previously sterile-filtered solution thereof.

In a particular embodiment, one or more compounds of the disclosure are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations should be apparent to those skilled in the art. The materials can also be obtained commercially from Alza Corporation and Nova Pharmaceuticals, Inc. Liposomal suspensions (including liposomes targeted to cells with monoclonal antibodies) can also be used as pharmaceutically acceptable carriers. These can be prepared according to methods known to those skilled in the art, for example, as described in U.S. Pat. No. 4,522,811.

The data obtained from the cell culture assays and animal studies can be used in formulating a range of dosage for use in humans. The dosage of such compounds lies within a range of circulating concentrations that include the ED50 with little or no toxicity. The dosage may vary within this range depending upon the dosage form employed and the route of administration utilized. For any compound used in the method of the disclosure, the therapeutically effective dose can be estimated initially from cell culture assays. A dose can be formulated in animal models to achieve a circulating plasma concentration range that includes the IC50 (e.g., the concentration of the test compound which achieves a half-maximal inhibition of symptoms) as determined in cell culture. Such information can be used to more accurately determine useful doses in humans. Levels in plasma can be measured, for example, by high performance liquid chromatography.

Compositions and formulations of one or more compounds disclosed herein can be used in combination with other active agents to treat a disorder or disease in a subject.

It should be understood that the administration of an additional therapeutic agent with a compound of the disclosure encompasses co-administration of these therapeutic agents in a substantially simultaneous manner, such as in a single capsule having a fixed ratio of active ingredients or in multiple, separate capsules for each active ingredient. In addition, administration of an additional therapeutic agent in combination with a compound disclosed herein also encompasses use of each type of therapeutic agent in a sequential manner. In either case, the treatment regimen will provide beneficial effects of the drug combination in treating the disorders described herein.

In a further embodiment, the compounds disclosed herein can be combined with one or more class of therapeutic agents, including, but not limited to, alkylating agents, cancer immunotherapy monoclonal antibodies, anti-metabolites, mitotic inhibitors, antitumor antibiotics, topoisomerase inhibitors, photosensitizers, tyrosine kinase inhibitors, anticancer agents, chemotherapeutic agents, anti-migraine treatments, anti-tussives, mucolytics, decongestants, anti-allergic non-steroidals, expectorants, antihistamine treatments, antiretroviral agents, CYP3A inhibitors, CYP3A inducers, protease inhibitors, adrenergic agonists, anticholinergics, mast cell stabilizers, xanthines, leukotriene antagonists, glucocorticoid treatments, antibacterial agents, antifungal agents, sepsis treatments, steroidals, local or general anesthetics, NSAIDS, NRIs, DARIs, SNRIs, sedatives, NDRIs, SNDRIs, monoamine oxidase inhibitors, hypothalamic phoshpholipids, antiemetics, ECE inhibitors, opioids, thromboxane receptor antagonists, potassium channel openers, thrombin inhibitors, growth factor inhibitors, anti-platelet agents, P2Y(AC) antagonists, anticoagulants, low molecular weight heparins, Factor VIa inhibitors, Factor Xa inhibitors, renin inhibitors, NEP inhibitors, vasopepsidase inhibitors, squalene synthetase inhibitors, anti-atherosclerotic agents, MTP inhibitors, calcium channel blockers, potassium channel activators, alpha-muscarinic agents, beta-muscarinic agents, anti-arrhythmic agents, diuretics, thrombolytic agents, anti-diabetic agents, mineralocorticoid receptor antagonists, growth hormone secretagogues, aP2 inhibitors, phophodiesterase inhibitors, anti-inflammatories, antiproliferatives, antibiotics, farnesyl-protein transferase inhibitors, hormonal agents, plant-derived products, epipodophyllotoxins, taxanes, prenyl-protein transferase inhibitors, anti-TNF antibodies and soluble TNF receptors, Cyclooxygenase-2 inhibitors, and miscellaneous agents.

For use in the therapeutic applications described herein, kits and articles of manufacture are also described herein. Such kits can comprise a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. The containers can be formed from a variety of materials such as glass or plastic.

For example, the container(s) can comprise one or more formulations described herein, optionally in a composition or in combination with another agent as disclosed herein. The container(s) optionally have a sterile access port (for example the container can be an intravenous solution bag or a vial having a stopper pierceable by a hypodermic injection needle). Such kits optionally comprise a compound with an identifying description or label or instructions relating to its use in the methods described herein.

A kit will typically comprise one or more additional containers, each with one or more of various materials (such as reagents, optionally in concentrated form, and/or devices) desirable from a commercial and user standpoint for use of a compound described herein. Non-limiting examples of such materials include, but are not limited to, buffers, diluents, filters, needles, syringes; carrier, package, container, vial and/or tube labels listing contents and/or instructions for use, and package inserts with instructions for use. A set of instructions will also typically be included.

A label can be on or associated with the container. A label can be on a container when letters, numbers or other characters forming the label are attached, molded or etched into the container itself, a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein. These other therapeutic agents may be used, for example, in the amounts indicated in the Physicians' Desk Reference (PDR) or as otherwise determined by one of ordinary skill in the art.

Methods

Provided herein are methods of treating inflammatory disorders, neoplasms, and cell proliferative disorders comprising contacting a subject or cell with any of the foregoing formulations. In embodiments, provided are methods of modulating the production or induction of inflammation and/or inflammatory cytokines comprising contacting a cell or subject with a formulation as described herein. In embodiments, the cell is a chondrocyte.

Traditionally, cartilage has been considered to be a static tissue, with little to no cellular turnover or capacity for repair following injury. However, detailed analysis of articular cartilage tissues from a variety of species has identified a primitive stem/progenitor chondrocyte population located within the layer of cartilage closest to the joint space, termed the superficial zone. These cells are capable of proliferating and producing hyaline matrix, and mouse lineage tracing studies show these cells maintain cartilage throughout life, but it is clear that they lack sufficient capacity to effect substantive regeneration in most injury contexts. Moreover, there is a paucity of information on how to positively identify these cells in humans and understand their biology. Finally, pro-inflammatory signaling that often accompanies cartilage injury is a major inhibitor of proliferation while also driving apoptosis.

The pathogenesis of osteoarthritis (OA) often begins from an injury to articular cartilage, which establishes chronic, low-grade inflammation mediated by interleukin-6/glycoprotein 130 (IL-6/gp130) and other factors that promote matrix degradation over time and eventual destruction of cartilage. IL-6 signaling through IL-6R/gp130 suppresses chondrocyte proliferation, promotes mineralization in articular cartilage, downregulation of matrix proteins and increases expression of matrix-degrading proteases. Moreover, blockade of IL-6 in vivo in mouse models of OA has been shown to be chondroprotective. Importantly, higher serum levels of IL-6 have been correlated with the development of OA in humans, and a monoclonal antibody against IL-6R is currently in Phase III clinical trials for the treatment of hand OA (NCT02477059). Signaling downstream of IL-6/gp130 is mediated by multiple pathways, including signal transducer and activator of transcription 3 (STAT3). STAT3 has been demonstrated to have pleiotropic effects during chondrogenesis and in articular chondrocytes. During chondrogenic differentiation of multipotent mesenchymal stem cells, IL-6/STAT3 signaling promotes chondrocyte commitment and matrix production. Similarly, loss of STAT3 during limb formation results in increased hypertrophy, premature ossification and decreases in expression of the master regulator of chondrocyte identity SOX9. In contrast, in adult articular chondrocytes inhibition of STAT3 downstream of IL-6 is chondroprotective, reducing the severity of OA-like pathology in a mouse model. Together, these data indicate that IL-6/STAT3 signaling can drive matrix loss and development of OA in vivo in both mouse models and humans.

Glycoprotein 130 (also known as gp130, IL6ST, IL6-beta or CD130) is a transmembrane protein which is the founding member of the class of all cytokine receptors. It forms one subunit of the type I cytokine receptor within the IL-6 receptor family. It is often referred to as the common gp130 subunit, and is important for signal transduction following cytokine engagement. It interacts with Janus kinases to elicit an intracellular signal following receptor interaction with its ligand.

Provided herein are methods of reducing activation of gp130 in a subject in need thereof by administering an effective amount of any of the formulations disclosed above.

Provided herein are methods of treating a subject for an inflammatory disorder by administering an effective amount of any of the formulations disclosed above. In embodiments, the inflammatory disorder is allergy, asthma, autoimmune disease, cancer, diabetes, inflammatory bowel disease (IBD), cardiovascular disease, nonalcoholic fatty liver disease (NFLD), non-alcoholic steatohepatitis (NASH), hepatitis, fibrosis, or cirrhosis. In embodiments, the disclosed formulations are administered directly into the joints to reduce inflammation.

Methods of treatment can include administering another agent suitable for treating any of the diseases described above. Methods can include administering, in addition to any of the above formulations, an effective amount of an alkylating agent, a cancer immunotherapy monoclonal antibody, an anti-metabolite, a mitotic inhibitor, an antitumor antibiotic, a topoisomerase inhibitor, a photosensitizer, a tyrosine kinase inhibitor, an anti-cancer agent, a chemotherapeutic agent, an anti-migraine treatment, an anti-tussive, a mucolytic, a decongestant, an anti-allergic non-steroidal, an expectorant, an antihistamine treatment, an anti-retroviral agent, a CYP3A inhibitor, a CYP3A inducer, a protease inhibitor, an adrenergic agonist, an anticholinergic, a mast cell stabilizer, a xanthine, a leukotriene antagonist, a glucocorticoid treatment, an antibacterial agent, an antifungal agent, a sepsis treatment, a steroidal, a local anesthetic, a general anesthetic, NSAID, NRI, DARI, SNRI, a sedative, NDRI, SNDRI, a monoamine oxidase inhibitor, a hypothalamic phoshpholipid, an antiemetics, an ECE inhibitor, an opioid, a thromboxane receptor antagonist, a potassium channel opener, a thrombin inhibitor, a growth factor inhibitor, an anti-platelet agents, a P2Y (AC) antagonist, an anticoagulant, low molecular weight heparin, a Factor Via inhibitor, a Factor Xa inhibitor, a renin inhibitor, a NEP inhibitor, a vasopepsidase inhibitor, a squalene synthetase inhibitor, an anti-atherosclerotic agent, a MTP inhibitor, a calcium channel blocker, a potassium channel activator, an alpha-muscarinic agent, a beta-muscarinic agent, an anti-arrhythmic agent, a diuretic, a thrombolytic agent, an anti-diabetic agent, a mineralocorticoid receptor antagonist, a growth hormone secretagogue, an aP2 inhibitor, a phodiesterase inhibitor, an anti-inflammatory, an antiproliferative, an antibiotic, a farnesyl-protein transferase inhibitor, a hormonal agent, a plant-derived product, an epipodophyllotoxin, a taxane, a prenyl-protein transferase inhibitor, an anti-TNF antibody, a soluble TNF receptor, or a cyclooxygenase-2 inhibitor.

Provided herein are methods for making any of the above formulations. In embodiments, solid CX-011 is added to a solution containing a non-ionic surfactant as provided above. In embodiments, the addition is performed with stirring. Apparatuses for stirring are well known in the art and include magnetic stirrers, overhead stirrers (e.g. impeller), vortexers, orbital shakers, and the like. The speed and vigor of stirring can be controlled. In embodiments, the dissolution is enhanced by sonication. Sonication can be used to speed dissolution, by breaking intermolecular interactions. Sonication is the act of applying sound energy to agitate particles in a sample. Ultrasonic frequencies (>20 kHz) can be used, leading to the process also being known as ultrasonication or ultra-sonication. Ultrasonication devices, e.g. ultrasonication baths and ultrasonication probes, are known in the art. Mixing can be for about 5 minutes, about 10 minutes, about 15 minutes, about 30 minutes, about one hour, about two hours, about four hours, about 8 hours, about 12 hours, about 24 hours, about 48 hours, or about 72 hours, or more.

Other variables to speed dissolution can be applied, such a modulation of temperature and pH.

Confirmation of dissolution can be confirmed by visual inspection, either by the naked eye or by microscope, to detect the presence of undissolved particles. Spectroscopic methods can also be used, such as light scattering detection or absorbance spectroscopy. Apparatuses for such spectroscopic detection are well-known in the art.

EXAMPLES

Example 1

Solid CX-011 (5 mg) was mixed in a solution of 20%-40% 2-Hydroxypropyl)-β-cyclodextrin (Accelachem) in water (10 mL) and the mixture sonicated for 30 minutes. Dissolution determined by visual inspection. Not soluble.

Example 2

Solid CX-011 (5 mg) was mixed in a solution of 20%-40% 2-Hydroxypropyl)-β-cyclodextrin (Accelachem) in water (10 mL) and 50 µL 1N HCl and the mixture sonicated for 30 minutes. Dissolution determined by visual inspection. Not soluble.

Example 3

Solid CX-011 (4 mg) was mixed in a solution of 3N HCl aqueous (2 mL) and the mixture sonicated for 30 minutes. Dissolution determined by visual inspection. Not soluble.

Example 4

Solid CX-011 (2.6 mg) was mixed in a solution of ~4N HCl in methanol (200 uL) and the mixture sonicated for 30 minutes. Dissolution determined by visual inspection. Not soluble.

Example 5

Solid CX-011 (6 mg) was mixed in a solution of $CH_2Cl_2$ and then 1 eq $MeSO_3H$ to obtain a clear solution. Solvent was evaporated. The remaining residue was washed with ether twice, then dried. The dried residue was mixed with water (10 mL) and the mixture sonicated for 30 minutes. Dissolution determined by visual inspection. Not soluble.

Example 6

Solid CX-011 (1 mg) was mixed in a solution of 10% polyvinylpyrrolidone K-30 (10 mL) and the mixture sonicated for 30 minutes. Dissolution determined by visual inspection. Not soluble.

Example 7

Solid CX-011 (1.5 mg) was mixed in ethanol (0.5 mL) and the mixture sonicated for 30 minutes. Dissolution determined by visual inspection. Not soluble.

Example 8

Solid CX-011 (3 mg) was mixed in in propylene glycol (0.5 mL) (Spectrum) and the mixture sonicated for 30 minutes. Dissolution determined by visual inspection. Not soluble.

Example 9

Solid CX-011 (4 mg) was added to DMA (0.5 mL) (Sigma) and mixed on a vortexer to obtain a clear solution. Water (0.5 mL) was added. Precipitation was observed upon visual inspection.

Example 10

Solid CX-011 (2.8 mg) was added to PEG400 (0.5 mL) (Spectrum) and mixed on a vortexer until dissolved. Water (0.5 mL) was added. Precipitation was observed upon visual inspection.

Example 11

Solid CX-011 (3.0 mg) was mixed in 30% Kolliphor® HS 15 (5 mL) (Sigma) and the mixture sonicated for 30 minutes. Dissolution determined by visual inspection. Dissolved—clear solution upon visual inspection.

Example 12

Solid CX-011 (15 mg) was mixed in polysorbate 80 (1 mL) and the mixture sonicated for 30 minutes. The solution was clear. Water (10 mL) was added and a precipitate was observed.

Example 13

Preparation of 30% (w/v) Kolliphor HS 15 in aqueous solution. Solid Kolliphor HS 15 was immersed in a water bath at 37° C. until melted. A 30% (w/v) solution was prepared by vortex mixing Kolliphor HS 15 with an appropriate amount of distilled water. The mixture was filtered through a 0.22 um PES filter (Corning).

Example 14

15 mg CX-011 was added to a 50 mL tube. A volume of 5-10 mL 30% kolliphor HS was added. The mixture was sonicated for 2 hours to obtain a clear solution. Distilled water or other physiology buffer, for example, PBS or saline was added to the above completely dissolved solution to final volume 100 mL with gently stirring. The solution can be filtered through 0.22 um filter. The appearance and pH value was noted. The solution was clear with pH value 5-5.5 for water and saline solution and is 7.2 for PBS solution. There was no significant difference of the concentration of CX-011 before or after filtration by checking UV absorbance at 323 nm. The final Kolliphor HS concentration in solution is about 1.5%-3%.

The solution remained clear after 1 week at room temperature. HPLC analysis indicated that the CX-011 compound was stable under preparation and storage.

Example 15

Formulation 1:
For 1 mL solution (water)
CS-011 150 ug
Kolliohor HS 15 (sigma 42966) 25 mg
Formulation 2:
For 1 mL solution (0.9% saline)
CS-011 150 ug
Kolliohor HS 15 (sigma 42966) 25 mg
NaCl 9 mg
Formulation 3:
For 1 mL solution (PBS)
CS-011 150 ug
Kolliohor HS 15 (sigma 42966) 25 mg
KCl 0.2 mg
KH2PO4 0.24 mg
NaCl 8.0 mg
Na2HPO4 1.44 mg

What is claimed is:

1. A formulation comprising CX-011 and a non-ionic surfactant, wherein CX-011 has formula wherein the formulation is an aqueous solution, wherein said non-ionic surfactant is about 1-5% w/v, and wherein said CX-011 concentration is at least about 50 µg/ml.

2. The formulation of claim 1, wherein said non-ionic surfactant is a polysorbate, an ethoxylate, ethoxylated amines and/or fatty acid amides, fatty acid esters of polyhydroxy compounds, a fatty acid ester of glycerol, a fatty acid ester of sucrose, or an alkyl polyglucoside.

3. The formulation of claim 1, wherein said non-ionic surfactant is a mixture of polyglycolated mono or di-ester of hydroxyl fatty acid and free polyethylene glycol.

4. The formulation of claim 1, wherein said non-ionic surfactant is Polyoxyl 15 Hydroxystearate, Polyoxyl castor oil, Polysorbate 80, Polysorbate 60, Polysorbate 40, or Polysorbate 20.

5. The formulation of claim 4, wherein said non-ionic surfactant is Polyoxyl 15 Hydroxystearate.

6. The formulation of claim 4, wherein said non-ionic surfactant is Polysorbate 80.

7. The formulation of claim 1, wherein said non-ionic surfactant is about 1-3% w/v.

8. The formulation of claim 1, wherein said non-ionic surfactant is about 1.5-3% w/v.

9. The formulation of claim 1, wherein said CX-011 concentration is at least about 150 µg/ml.

10. A pharmaceutical composition comprising the formulation of claim 1 and a pharmaceutical excipient.

11. A method of reducing activation of gp130 in a subject in need thereof, said method comprising administering to said subject an effective amount of the formulation of claim 1.

12. A method of treating an inflammatory disorder in a subject in need thereof, said method comprising administering to said subject an effective amount of the formulation of claim 1.

13. The method of claim 12, wherein said inflammatory disorder is an autoimmune disease, arthritis, rheumatoid arthritis, osteoarthritis, psoriatic arthritis, juvenile idiopathic arthritis, multiple sclerosis, systemic lupus erythematosus (SLE), myasthenia gravis, juvenile onset diabetes, diabetes mellitus type 1, graft-versus-host disease (GvHD), Guillain-Barre syndrome, Hashimoto's encephalitis, Hashimoto's thyroiditis, ankylosing spondylitis, psoriasis, Sjogren's syndrome,vasculitis, glomerulonephritis, auto-immune thyroiditis, Behcet's disease, Crohn's disease, ulcerative colitis, bullous pemphigoid, sarcoidosis, ichthyosis, Graves ophthalmopathy, inflammatory bowel disease, Addison's disease, Vitiligo, asthma, allergic asthma, acne vulgaris, celiac disease, chronic prostatitis, inflammatory bowel disease, pelvic inflammatory disease, reperfusion injury, ischemia reperfusion injury, stroke, sarcoidosis, transplant rejection, interstitial cystitis, atherosclerosis, scleroderma, or atopic dermatitis.

14. The method of claim 12, wherein said inflammatory disorder is osteoarthritis of the knee or temporomandibular joint osteoarthritis.

15. The method of claim 14, wherein the formulation is administered intraarticularly.

16. A method of treating cancer in a subject in need thereof, said method comprising administering to said subject an effective amount of the formulation of claim 1.

17. The method of claim 15, further comprising administering an effective amount of an alkylating agent, a cancer immunotherapy monoclonal antibody, an anti-metabolite, a mitotic inhibitor, an antitumor antibiotic, a topoisomerase inhibitor, a photosensitizer, a tyrosine kinase inhibitor, an anti-cancer agent, a chemotherapeutic agent, an anti-migraine treatment, an anti-tussive, a mucolytic, a decongestant, an anti-allergic non-steroidal, an expectorant, an anti-histamine treatment, an anti-retroviral agent, a CYP3A inhibitor, a CYP3A inducer, a protease inhibitor, an adrenergic agonist, an anticholinergic, a mast cell stabilizer, a xanthine, a leukotriene antagonist, a glucocorticoid treatment, an antibacterial agent, an antifungal agent, a sepsis treatment, a steroidal, a local anesthetic, a general anesthetic, NSAID, NRI, DARI, SNRI, a sedative, NDRI, SNDRI, a monoamine oxidase inhibitor, a hypothalamic phoshpholipid, an antiemetics, an ECE inhibitor, an opioid, a thromboxane receptor antagonist, a potassium channel opener, a thrombin inhibitor, a growth factor inhibitor, an anti-platelet agents, a P2Y (AC) antagonist, an anticoagulant, low molecular weight heparin, a Factor Via inhibitor, a Factor Xa inhibitor, a renin inhibitor, a NEP inhibitor, a vasopepsidase inhibitor, a squalene synthetase inhibitor, an anti-atherosclerotic agent, a MTP inhibitor, a calcium channel blocker, a potassium channel activator, an alpha-muscarinic agent, a beta-muscarinic agent, an anti-arrhythmic agent, a diuretic, a thrombolytic agent, an anti-diabetic agent, a mineralocorticoid receptor antagonist, a growth hormone secretagogue, an aP2 inhibitor, a phophodiesterase inhibitor, an anti-inflammatory, an antiproliferative, an antibiotic, a farnesyl-protein transferase inhibitor, a hormonal agent, a plant-derived product, an epipodophyllotoxin, a taxane, a prenyl-protein transferase inhibitor, an anti-TNF antibody, a soluble TNF receptor, or a cyclooxygenase-2 inhibitor. sonication. one hour.

18. A method of solubilizing CX-011, wherein CX-011 has formula

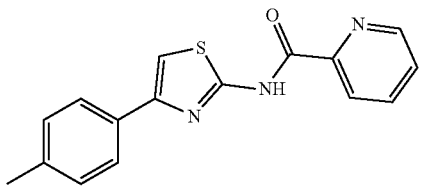 [SMILES: Cc1ccc(-c2csc(NC(=O)c3ccccn3)n2)cc1]

and wherein the method comprises:
a. combining CX-011 with an aqueous solution of 3-30% non-ionic surfactant;
b. subjecting said combination to mixing until CX-011 is dissolved.

19. The method of claim 16, wherein said mixing comprises sonication.

20. The method of claim 17, wherein said sonication is for about one hour.

21. The method of claim 16, further comprising determining whether CX-011 is dissolved.

22. The method of claim 19, wherein said determining is performed by visual inspection, light scattering, UV absorbance, or quantitative HPLC.

* * * * *